United States Patent
Lu et al.

(10) Patent No.: US 12,227,759 B2
(45) Date of Patent: Feb. 18, 2025

(54) TEMPERATURE-SENSITIVE CELL CULTURE COMPOSITION, METHOD FOR USING THE SAME, METHOD FOR FORMING THE SAME, AND USE THEREOF

(71) Applicant: Industrial Technology Research Institute, Hsinchu (TW)

(72) Inventors: Chia-Jung Lu, Taichung (TW); Jing-En Huang, Hsinchu (TW); Liang-Cheng Su, Kaohsiung (TW); Hsin-Hsin Shen, Zhudong Township (TW); Yuchi Wang, New Taipei (TW); Ying-Hsueh Chao, Zhubei (TW); Li-Hsin Lin, Zhubei (TW); Hsiu-Hua Huang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 736 days.

(21) Appl. No.: 17/126,942

(22) Filed: Dec. 18, 2020

(65) Prior Publication Data
US 2021/0269765 A1 Sep. 2, 2021

Related U.S. Application Data

(60) Provisional application No. 62/951,314, filed on Dec. 20, 2019.

(51) Int. Cl.
| | | |
|---|---|---|
| *C12N 5/00* | (2006.01) | |
| *A61K 9/00* | (2006.01) | |
| *A61K 35/12* | (2015.01) | |
| *A61K 47/38* | (2006.01) | |
| *A61K 47/42* | (2017.01) | |

(52) U.S. Cl.
CPC .......... *C12N 5/0018* (2013.01); *A61K 9/0024* (2013.01); *A61K 35/12* (2013.01); *A61K 47/38* (2013.01); *A61K 47/42* (2013.01); *C12N 2523/00* (2013.01); *C12N 2533/40* (2013.01); *C12N 2533/54* (2013.01); *C12N 2533/78* (2013.01); *C12N 2539/00* (2013.01)

(58) Field of Classification Search
None
See application file for complete search history.

(56) References Cited

U.S. PATENT DOCUMENTS

| | | | |
|---|---|---|---|
| 10,449,272 B2 * | 10/2019 | Wang | A61L 31/145 |
| 2012/0020932 A1 | 1/2012 | Yao et al. | |
| 2019/0030211 A1 | 1/2019 | Nam et al. | |

FOREIGN PATENT DOCUMENTS

| | | |
|---|---|---|
| TW | 1245634 B | 12/2005 |
| TW | 1668002 B | 8/2019 |

OTHER PUBLICATIONS

Brun-Graeppi et al., "Thermoresp ive surfaces for cell culture and enzyme-free cell detachment," Progress in Polymer Science, vol. 35, No. 11, Jul. 27, 2010, pp. 1311-1324.

Taiwanese Office Action and Search Report for Taiwanese Application No. 109144984, dated Feb. 25, 2022.

* cited by examiner

*Primary Examiner* — Anand U Desai
(74) *Attorney, Agent, or Firm* — Birch, Stewart, Kolasch & Birch, LLP (57) ABSTRACT

A temperature-sensitive cell culture composition is provided. The temperature-sensitive cell culture composition includes a hydrogel, a cellulose, a gelatin and a collagen. Based on 1 part by weight of the collagen, a content of the hydrogel is between 0.03 parts by weight and 60 parts by weight, a content of the cellulose is between 150 parts by weight and 360 parts by weight, and a content of the gelatin is between 21 parts by weight and 12 parts by weight. In addition, a method for using the temperature-sensitive cell culture composition, a method for forming the temperature-sensitive cell culture composition, and a use of the temperature-sensitive cell culture composition are also provided.

16 Claims, 6 Drawing Sheets
(2 of 6 Drawing Sheet(s) Filed in Color)

TEMPERATURE-SENSITIVE CELL CULTURE COMPOSITION, METHOD FOR USING THE SAME, METHOD FOR FORMING THE SAME, AND USE THEREOF

CROSS REFERENCE TO RELATED APPLICATION

This application claims the benefit of U.S. Provisional Application No. 62/951,314, filed on Dec. 20, 2019, the entirety of which is incorporated by reference herein.

BACKGROUND

Technical Field

The present disclosure is related to a temperature-sensitive cell culture composition, and is particularly related to a temperature-sensitive cell culture composition can be used as a cell carrier, and method for using the same, method for forming the same, and use thereof.

Description of the Related Art

After cell culturing by using traditional cell culture medium, the processing steps such as separation and purification are usually required to remove the cells from the culture medium for subsequent use. For example, processing steps such as trypsin or cell scrapper are used to separate and purify cells. Moreover, for medical applications, the collected foregoing cells need to be mixed with cell carriers for subsequent applications. For example, the collected cells need to be mixed with a biocompatible sustained-release material before applying to an individual.

In response to the widespread application of cell culture materials, the development of cell culture materials is still one of the research goals of the industry which is fully dedicated.

SUMMARY

According to some embodiments of the present disclosure, a temperature-sensitive cell culture composition, comprising: a hydrogel, a cellulose, a gelatin, and a collagen, wherein based on 1 part by weight of the collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight is provided.

According to some embodiments of the present disclosure, a method for using a temperature-sensitive cell culture composition, comprising: adding a cell to the forgoing temperature-sensitive cell culture composition at a first temperature; and performing cell culture at a second temperature is provided.

According to some embodiments of the present disclosure, a method for forming a temperature-sensitive cell culture composition, comprising: mixing a hydrogel and a cellulose at a first temperature, allowing to stand for a first time interval at a second temperature to form a gel substrate; and adding a mixture of a collagen and a gelatin to the gel substrate; wherein based on 1 part by weight of the collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight.

According to some embodiments of the present disclosure, a use of a foregoing temperature-sensitive cell culture composition, wherein the foregoing temperature-sensitive cell culture composition is used for cell transplantation or cell therapy is provided.

A detailed description is given in the following embodiments with reference to the accompanying drawings.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION

The following is a detailed description of the temperature-sensitive cell culture composition provided in the embodiments of the present disclosure. The embodiments of the disclosure can be understood with reference to the accompanying drawings, and the drawings of the disclosure are also regarded as part of the disclosure description. It should be understood that the drawings of the present disclosure are not drawn to scale. In fact, the size of the elements may be arbitrarily enlarged or reduced in order to clearly show the features of the present disclosure.

In the present disclosure, the terms "about", "approximately", and "substantially" usually mean within 5%, or within 3%, or within 2%, or within 1%, or within 0.5% of a given value or range. The approximate quantity given in the present disclosure, that is, the meaning of "about", "approximately", "substantially" can still be implied without specifying "about", "approximately", "substantially".

Unless otherwise defined, all terms (including technical and scientific terms) used in the present disclosure have the same meanings as commonly understood by those skilled in the art to which the disclosure belongs. It is understandable that these terms, such as those defined in commonly used dictionaries, should be interpreted as having meaning consistent with the relevant technology and the background or context of this disclosure, and should not be interpreted in an idealized or excessively formal way, unless specifically defined in the embodiments of the disclosure.

According to some embodiments of the present disclosure, the temperature-sensitive cell culture composition with a specific formula has good biocompatibility and temperature-sensitive phase transition properties, and is easy to operate in cell culture experiments and subsequent applications. Also, it can be used directly as a cell carrier without separation and purification steps, so that the damage to cells caused by traditional cell separation and purification steps was avoided, and the convenience of related applications after cell culture can be effectively improved as well.

According to some embodiments of the present disclosure, a temperature-sensitive cell culture composition is provided, the temperature-sensitive cell culture composition comprising hydrogel, cellulose, gelatin, and collagen, but it is not limited thereto.

According to some embodiments, based on 1 part by weight of the collagen, a content of the hydrogel in the temperature-sensitive cell culture composition is between about 0.03 parts by weight and about 60 parts by weight, or about 0.33 parts by weight and about 33 parts by weight, for example, 0.5 parts by weight, 1 part by weight, 5 parts by weight, 10 parts by weight, 15 parts by weight, 20 parts by weight, 25 parts by weight, 30 parts by weight, 35 parts by weight, 40 parts by weight, 45 parts by weight, 50 parts by weight, or 55 parts by weight, but it is not limited thereto. According to some embodiments, the hydrogel may provide temperature-sensitive phase transition properties of the composition in a specific range of formula as mentioned above, for example, the phase change properties between liquid state and colloid state or the temperature-sensitive gelation properties.

According to some embodiments, the average molecular weight of the hydrogel may between about 2000 to about 6000, for example, about 3000, about 3500, about 4000, about 4500, about 5000 or about 5500, but it is not limited thereto.

In detail, according to some embodiments, hydrogel may having a structure represented by Formula (I) or Formula (II) shown as follows:

$$A\text{-}B\text{—}BOX\text{—}B\text{-}A, \quad \text{Formula (I); or}$$

$$B\text{-}A\text{-}B\text{—}(BOX\text{-}BAB)n\text{-}BOX\text{—}B\text{-}A\text{-}B, \quad \text{Formula (II),}$$

wherein the polymer block A is a hydrophilic polyethylene glycol polymer, the polymer block B is a hydrophobic polyester polymer, BOX is a bifunctional group monomer of 2,2'-Bis(2-oxazoline) for coupling di-block of A-B or tri-block of B-A-B, and n is an integer greater than or equal to 0.

According to some embodiments, the polymer block A, for example, may comprises polyethylene glycol (PEG) or methoxy-poly(ethylene glycol) (mPEG), but it is not limited thereto. According to some embodiments, the polymer block B, for example, may comprises poly(lactide-co-glycolide) (PLGA), poly(propionic-co-lactic) (PPLA), poly(valeric-co-lactic) (PVLA) or poly(caproic-co-lactic) (PCLA), but it is not limited thereto.

Moreover, according to some embodiments, based on 1 part by weight of the collagen, a content of the cellulose in the temperature-sensitive cell culture composition is between about 150 parts by weight and about 360 parts by weight, or about 166 parts by weight and about 333 parts by weight, for example, 170 parts by weight, 180 parts by weight, 190 parts by weight, 200 parts by weight, 210 parts by weight, 220 parts by weight, 230 parts by weight, 240 parts by weight, 250 parts by weight, 260 parts by weight, 270 parts by weight, 280 parts by weight, 290 parts by weight, 300 parts by weight, 310 parts by weight, 320 parts by weight, 330 parts by weight, 340 parts by weight, or 350 parts by weight, but it is not limited thereto. According to some embodiments, the cellulose may provide the cell carrier function of the composition in a specific range of formula as mentioned above.

According to some embodiments, the average molecular weight of the cellulose may between about 10000 to about 30000, for example, about 14000, about 15000, about 20000 or about 25000, but it is not limited thereto.

In detail, according to some embodiments, the cellulose may comprises methyl cellulose or other suitable cellulose, but it is not limited thereto. According to some embodiments, the rate of methyl substitution of methyl cellulose may between 25% and 35%, for example, between 27.5% and 31.5%, but it is not limited thereto.

Furthermore, according to some embodiments, based on 1 part by weight of the collagen, a content of the gelatin in the temperature-sensitive cell culture composition is between about 1 part by weight and about 12 parts by weight, or about 3 parts by weight and about 10 parts by weight, for example, 4 parts by weight, 5 parts by weight, 6 parts by weight, 7 parts by weight, 8 parts by weight or 9 parts by weight, but it is not limited thereto. According to some embodiments, the gelatin and the collagen may provide the extracellular matrix properties of the composition in a specific range of formula as mentioned above.

According to some embodiments, the average molecular weight of the gelatin may between about 100 kDa to about 200 kDa or between about 80 kDa to about 200 kDa, but it is not limited thereto. According to some embodiments, the average molecular weight of the collagen may between about 200 kDa to about 500 kDa, for example, about 100 kDa or about 300 kDa, but it is not limited thereto.

In detail, according to some embodiments, the collagen may comprise atelocollagen or other suitable collagen, but it is not limited thereto.

In addition, according to some embodiments, the temperature-sensitive cell culture composition may further comprise a medium, and the medium may comprise amino acids, vitamins, serum, antibiotics, a combination thereof or other suitable medium materials, but it is not limited thereto. In different embodiments, any suitable medium material may be selected according to the type of cells to be cultured. According to some embodiments, the temperature-sensitive cell culture composition may further comprise water, for example, ultrapure water.

For example, according to some embodiments, the foregoing medium may comprise minimal essential medium (MEM), Dulbecco's modified minimal essential medium (DMEM), non-essential amino acids solution, fetal bovine serum (FBS), horse serum, human serum (e.g., platelet rich plasma (PRP)), penicillin, streptomycin or other suitable medium materials, but it is not limited thereto.

According to the embodiments of the present disclosure, the temperature-sensitive cell culture composition in the foregoing specific range of formula has temperature-sensitive phase transition properties, and it may be a liquid at the first temperature range, and may be a gel at the second temperature range. According to some embodiments, the first temperature range may be between about 0° C. and about 32° C., and the second temperature range may be greater than about 32° C., for example, between about 33° C. and about 40° C. It should be noted that, according to some embodiments, the liquid-gel phase transition temperature of the temperature-sensitive cell culture composition may be about 32° C. to 40° C. The temperature-sensitive cell culture composition is a liquid at room temperature (e.g., 25° C.), and is a gel in the normal cell culture temperature range (e.g., 37° C.). Therefore, it is easy to operate when it is a liquid at room temperature, and 3D cell culture can be performed at the culture temperature to improve the culture efficiency.

In detail, according to some embodiments of the present disclosure, a method for using a temperature-sensitive cell culture composition is provided, including the following steps: adding cells to the foregoing temperature-sensitive cell culture composition at a first temperature, and performing cell culture at a second temperature. As mentioned above, the temperature-sensitive cell culture composition is a liquid at the first temperature and a gel at the second temperature. In addition, according to some embodiments, after the cell culture is performed at the second temperature, the temperature-sensitive cell culture composition may be loaded into the appliance at the first temperature for subsequent use. For example, according to some embodiments, the temperature-sensitive cell culture composition may be administered to an individual, such as a human.

According to some embodiments, the foregoing cells may include stem cells, immune cells, somatic cells, other suitable cells, or a combination thereof. According to some embodiments, the foregoing appliance may include a syringe, an injector, etc., but is not limited thereto. It is worth noting that according to the embodiments of the present disclosure, the temperature-sensitive cell culture composition with the foregoing specific formula may be used directly as a cell carrier without the steps of separation and purification. For example, the appliance may be used directly to apply the temperature-sensitive cell culture composition to an individual after the cell culture is completed, which may avoid damages to the cells caused by traditional cell separation and purification steps, and the efficiency and quality of related applications after the cell culture may significantly improve.

Figure 1:
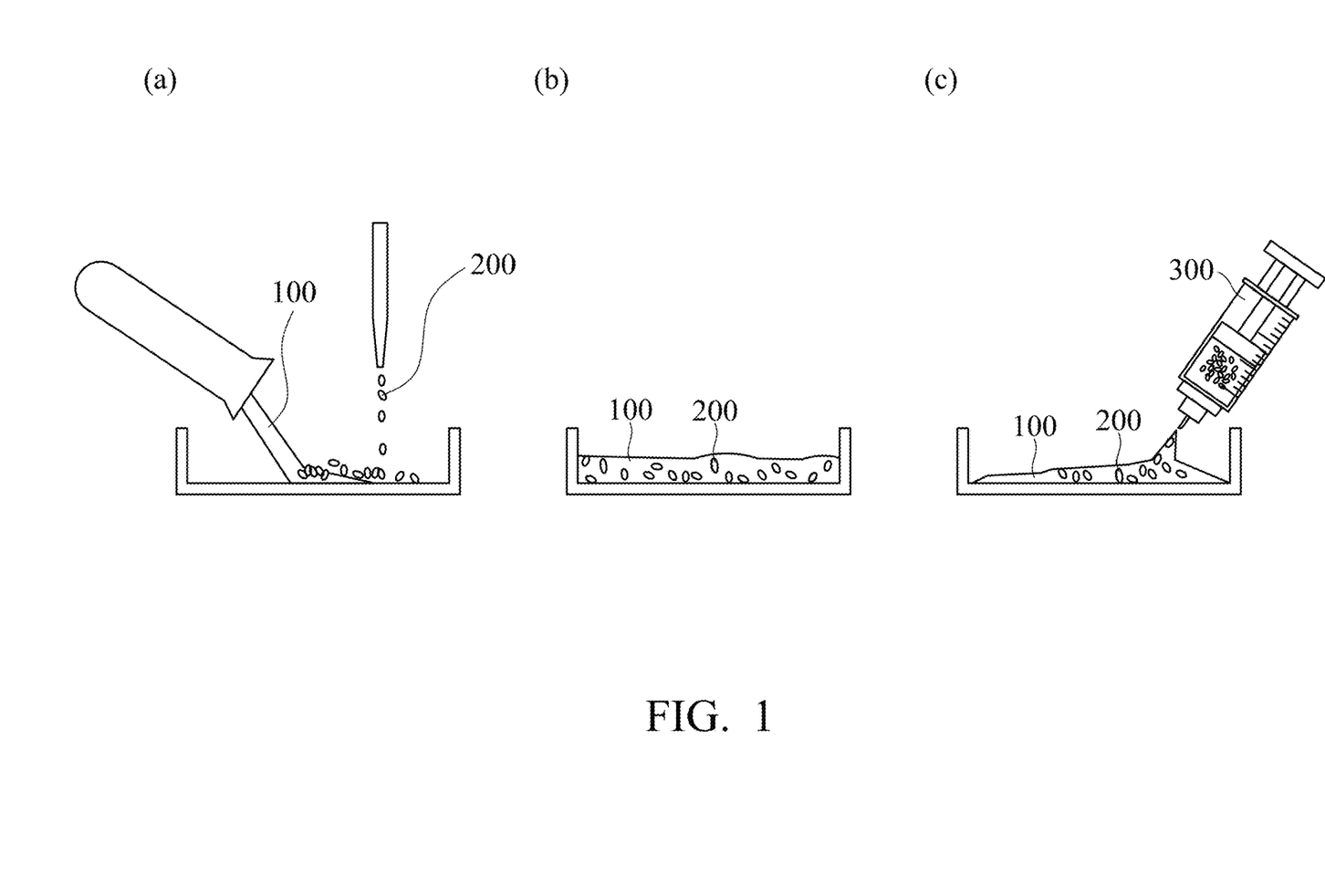
FIG. 1 shows a schematic diagram of a method for forming and using a temperature-sensitive cell culture composition according to some embodiments of the present disclosure.

In addition, according to some embodiments of the present disclosure, a method for forming a temperature-sensitive cell culture composition is further provided. Specifically, please refer to FIG. 1, FIG. 1 shows a schematic diagram of a method for forming and using a temperature-sensitive cell culture composition in some embodiments of the present disclosure. According to some embodiments, the temperature-sensitive cell culture composition 100 in which all components have been well mixed in advance may be added to the culture container at the first temperature, and the cells 200 are added to the culture container (as shown in step (a)), and then the medium 100c (not shown) may be added at the second temperature for cell culture. That is, the cells 200 may be cultured in a gel state of the temperature-sensitive cell culture composition 100 (as shown in step (b)). According to some embodiments, the temperature may be reduced to a first temperature after the cell culture is completed, and the temperature-sensitive cell culture composition 100 and cells 200 in liquid state are loaded into the appliance 300 at the first temperature for subsequent use ((As shown in step (c)).

According to some embodiments, the temperature-sensitive cell culture composition 100 in which all components have been well mixed in advance in advance may comprise hydrogel, cellulose, gelatin, and collagen, wherein based on 1 part by weight of the collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight.

Figure 2:
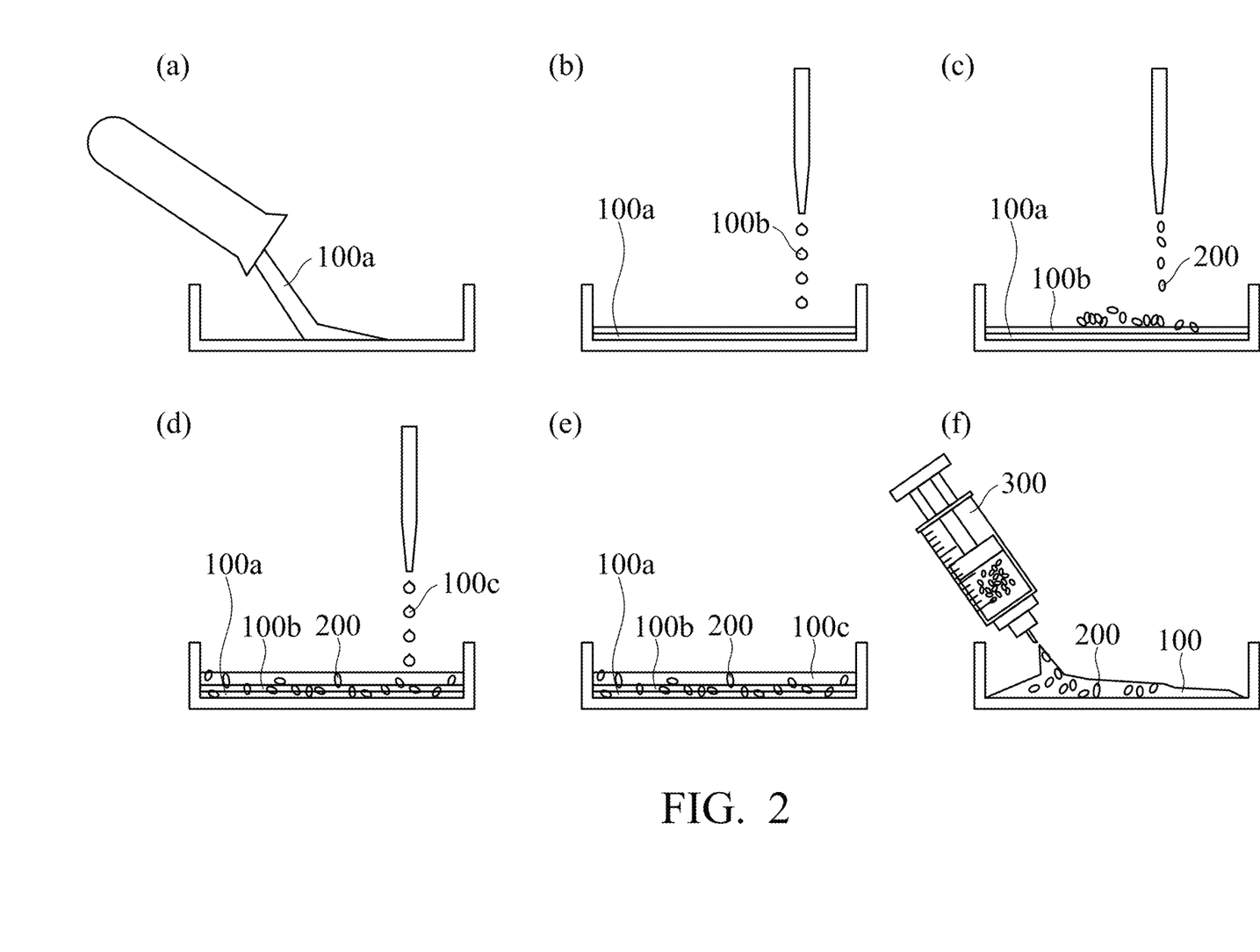
FIG. 2 shows a schematic diagram of a method for forming and using a temperature-sensitive cell culture composition according to some embodiments of the present disclosure.

Next, please refer to FIG. 2, FIG. 2 shows a schematic diagram of a method for forming and using a temperature-sensitive cell culture composition according to other embodiments of the present disclosure. As shown in FIG. 2, according to some embodiments, the first part 100a (e.g., containing hydrogel and cellulose) of the temperature-sensitive cell culture composition may be mixed at the first temperature and added to the culture container (as shown in step (a)), and then standing at a second temperature for the first time interval to form a gel substrate. And then, the mixture of the second part 100b (e.g., containing collagen and gelatin) of the temperature-sensitive cell culture composition may be added on the gel substrate formed by the foregoing first part 100a (as shown in step (b)). According to some embodiments, the range of the first time interval may be between 1 hour and 24 hours, or between 6 hours and 24 hours, or between 6 hours and 12 hours, for example, 7 hours, 8 hours, 9 hours, 10 hours or 11 hours.

According to some embodiments, the first part 100a of the temperature-sensitive cell culture composition may comprise hydrogel and cellulose, and the second part 100b may comprise collagen and gelatin, wherein based on 1 part by weight of collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight.

According to some embodiments, after the mixture of collagen and gelatin of the second part 100b is added to the gel substrate, it is allowed to stand at a second temperature for a second time interval, so that the mixture of collagen and gelatin forms a gel layer. According to some embodiments, the range of the second time interval may be between 2 hours and 12 hours, or between 2 hours and 6 hours, for example, 3 hours, 4 hours, or 5 hours. According to some embodiments, after the formation of the gel layer, the cells 200 may be added to the culture container (as shown in step (c)), then the medium 100c may be added to the gel layer, wherein the medium 100c may be a liquid (as shown in step (d)). After that, the cell culture may be performed at the second temperature. In detail, cells 200 may be cultured under the condition that the first part 100a and the second part 100b are in gel state and the medium 100c is in liquid state (as shown in step (e)). According to some embodiments, the temperature may be reduced to a first temperature after the cell culture is completed, and the temperature-sensitive cell culture composition 100 (including the first part 100a, the second part 100b and the medium 100c) and cells 200 in liquid state are loaded into the appliance 300 at the first temperature for subsequent use (as shown in step (f)). As mentioned above, according to some embodiments, cells may be cultured in the temperature-sensitive cell culture composition in which gel and liquid coexist.

In addition, according to some embodiments of the present disclosure, a use of the foregoing temperature-sensitive cell culture composition is also provided, which is used for cell transplantation or cell therapy. According to some embodiments, the temperature-sensitive cell culture composition may be further added with any suitable therapeutic agent, for example, a drug or growth factor, etc., to provide better therapeutic effect.

In order to make the above content and other objects, features, and advantages of the present disclosure more comprehensible, the following describes the examples, comparative examples, preparation examples and test examples in detail as follows, but they are not intended to limit the present disclosure.

Hybrid Rheometer Test

Test Examples 1~13

First, the compositions of Test examples 1~13 were prepared according to the content of methyl cellulose (average molecular weight of 15000), hydrogel (average molecular weight of 3500) and ultrapure water shown in Table 1, wherein the structure of the hydrogel was A-B—BOX—B-A. In addition, a hybrid rheometer (Discovery Hybrid Rheometers HR-2) was used to measure the storage modulus (storage modulus E') and loss modulus (Loss Modulus E") of the compositions of test examples 1~13, and the suitable range for cell culture test based on the data was selected. The measurement conditions of the hybrid rheometer were as follows: the fixture is a 40 mm flat plate, the temperature range is 0° C.~50° C., the temperature change speed is 2° C./min, the frequency is 1 Hz. The combination of the conditions of the loss modulus less than 6 Pa at 0° C.~25° C., and the storage modulus greater than 1 Pa at 37° C. was selected for the subsequent cell recovery test, because the composition material which meets this range had the characteristics of temperature-sensitive gel and was easy to operate at room temperature.

TABLE 1

| Test example | Methyl cellulose (parts by weight) | Hydrogel (parts by weight) | Water (parts by weight) | 0° C.~25° C. E" < 6 Pa | 37° C. E' > 1 Pa | Perform cell recovery test |
|---|---|---|---|---|---|---|
| 1 | 66.67 | 0.33 | 3266 | YES | NO | NO |
| 2 | 66.67 | 33.33 | 3233 | YES | NO | NO |
| 3 | 166.67 | 0.033 | 3167 | YES | NO | NO |
| 4 | 166.67 | 0.33 | 3166 | YES | YES | YES |
| 5 | 266.67 | 0.033 | 3067 | YES | YES | YES |
| 6 | 266.67 | 0.33 | 3066 | YES | YES | YES |
| 7 | 266.67 | 3.33 | 3063 | YES | YES | YES |
| 8 | 266.67 | 33.33 | 3033 | YES | YES | YES |
| 9 | 266.67 | 66.67 | 3000 | YES | YES | YES |
| 10 | 333.33 | 33.33 | 2967 | YES | YES | YES |
| 11 | 333.33 | 66.67 | 2933 | YES | YES | YES |
| 12 | 500 | 0.33 | 2833 | NO | YES | NO |
| 13 | 500 | 33.33 | 2800 | NO | YES | NO |

Test Examples 14~15

The compositions of Test examples 14~15 were prepared according to the content of hydrogel (average molecular weight of 3500), hydroxypropyl methylcellulose cellulose, HPMC) (average molecular weight of 86000), sodium carboxymethyl cellulose (2% 420 cP) and ultrapure water shown in Table 2. In addition, a hybrid rheometer (Discovery Hybrid Rheometers HR-2) was used to measure the storage modulus (storage modulus E') and loss modulus (Loss Modulus E') of the compositions of test examples 14~15, and the suitable range for cell culture test based on the data was selected. The measurement conditions of the hybrid rheometer were as follows: the fixture is a 40 mm flat plate, the temperature range is 0° C.~50° C., the temperature change speed is 2° C./min, the frequency is 1 Hz. The combination of the conditions of the loss modulus less than 6 Pa at 0° C.~25° C., and the storage modulus greater than 1 Pa at 37° C. was selected for the subsequent cell recovery test, because the composition material which meets this range had the characteristics of temperature-sensitive gel and was easy to operate at room temperature.

TABLE 2

| Test example | Hydrogel (parts by weight) | Hypromellose (parts by weight) | Sodium carboxymethyl cellulose (parts by weight) | Water (parts by weight) | 0° C.~25° C. E" < 6 Pa | 37° C. E' > 1 Pa | Perform cell recovery test |
|---|---|---|---|---|---|---|---|
| 14 | 0.33 | 83.33 | 0 | 3250 | YES | NO | NO |
| 15 | 0.33 | 0 | 56.67 | 3276 | YES | NO | NO |

According to the results of the hybrid rheometer test in Table 1 and Table 2, it is known that the compositions of Test examples 4~11 have a change of gelation in the temperature range about 37° C., that is, the combination of methyl cellulose and hydrogel in the range of specific ratio has the temperature-sensitive gelation properties. Moreover, the compositions of Test examples 14-15 using hypromellose or sodium carboxymethyl cellulose do not have temperature-sensitive gelation properties.

Figure 3:
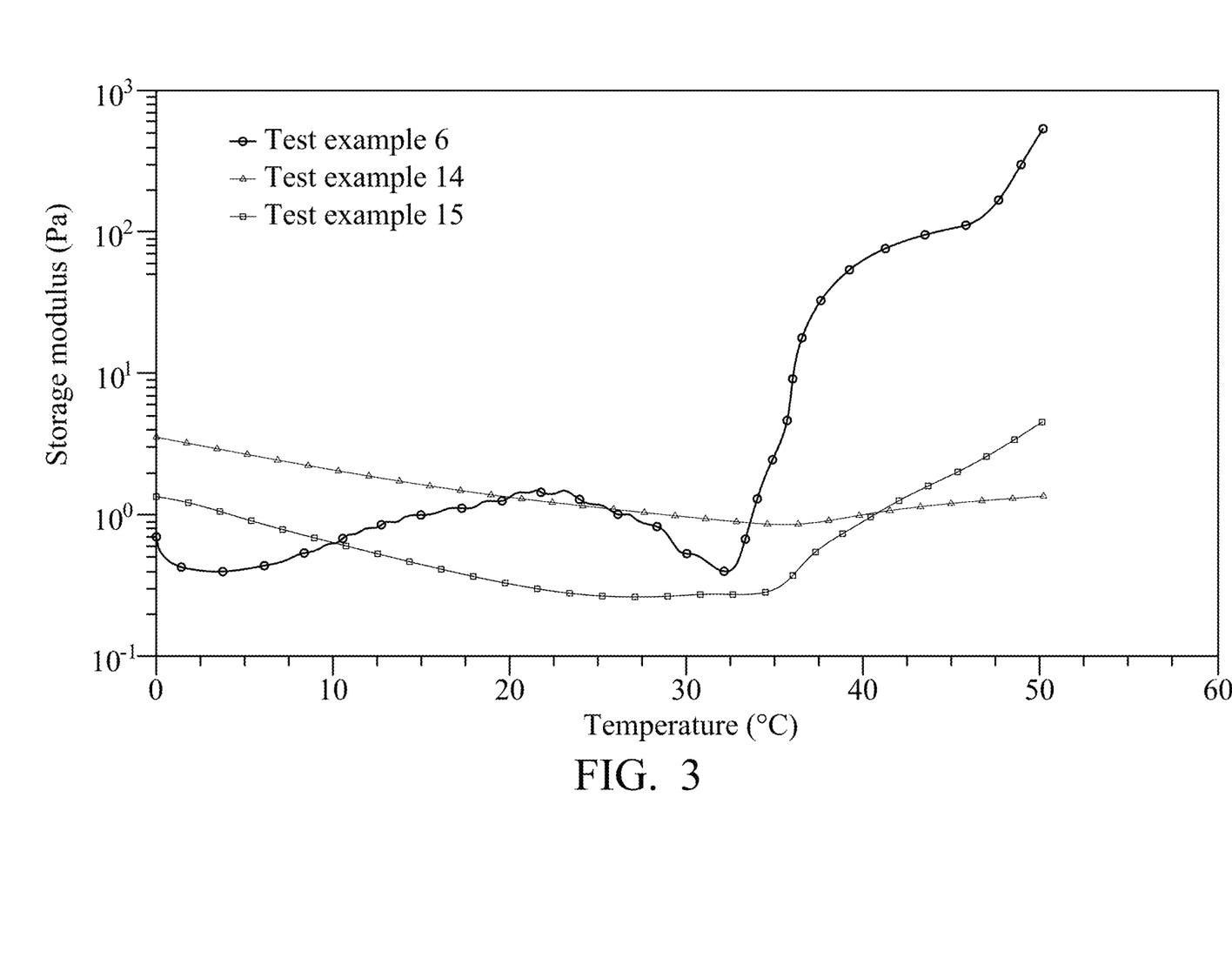
FIG. 3 shows the results of measuring the temperature-sensitive cell culture composition by using a hybrid rheometer according to some embodiments of the present disclosure.
Figure 4:
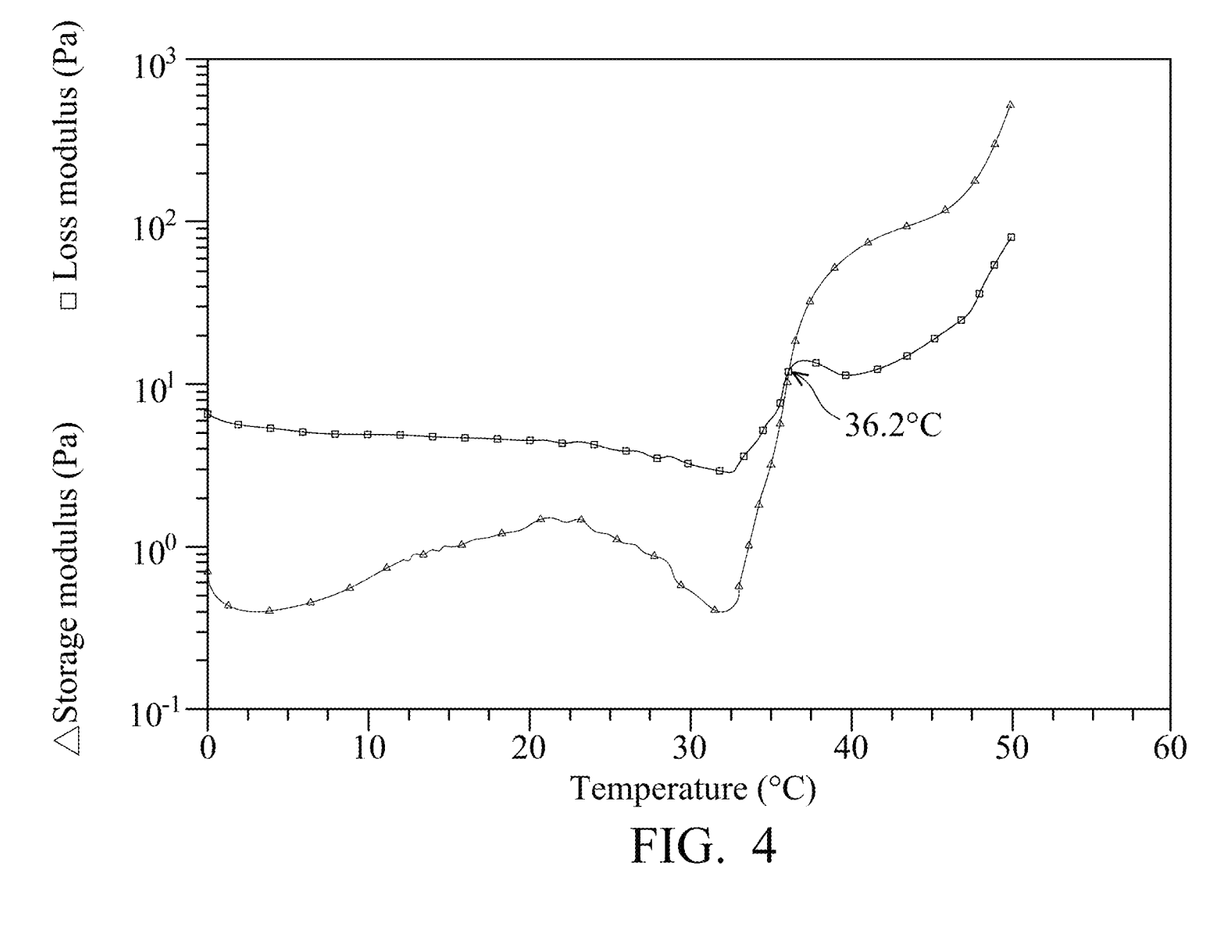
FIG. 4 shows the results of measuring the temperature-sensitive cell culture composition by using a hybrid rheometer according to some embodiments of the present disclosure.

Specifically, please refer to FIG. 3, the results of the hybrid rheometer test of the composition of Test example 6, Test example 14, and Test example 15 were shown in FIG. 3. As shown in FIG. 3, the composition of Test example 6 comprising methylcellulose and water has the gelation phenomenon in the range of 32° C. to 40° C., while the compositions of Test Example 14~15 comprising hypromellose or sodium carboxymethyl cellulose do not have the gelation phenomenon. Moreover, the measurement results of the storage modulus and loss modulus of the composition of Test example 6 were further shown in FIG. 4. As shown in FIG. 4, the two curves of storage modulus and loss modulus are crossover at 36.2° C.

Cell Viability Test

Examples 1~3 and Comparative Examples 1~2

Next, the composition of the foregoing Test example 6 (comprising 266.67 parts by weight of methyl cellulose and 0.33 parts by weight of hydrogel) was gelled at 37° C. and dried for 6~24 hours, then the contents of atelocollagen (average molecular weight of 300 kDa) and gelatin (average molecular weight of between about 100 kDa and about 200 kDa) shown in Table 3 were added to further prepare the compositions of Examples 1~3 and Comparative examples 1~2. After standing in a 37° C. incubator for 2~6 hours, NCTC clone 929 cells (purchased from ATCC manufacturer) and the medium were added. The medium contains minimal essential medium MEM (purchased from Gibco manufacturer), 10% FBS (purchased from Gibco manufacturer), 1% penicillin-streptomycin (from Gibco manufacturer), and non-essential amino acids solution (from Gibco manufacturer). Then, cultured by aeration in 95% air and 5% carbon dioxide for 4 days, and after the 4 days, the cells were recovered and tested for cell viability. The results are shown in Table 3.

In addition, the method of cell recovery includes the following steps: the gel-like composition was cooled down to 4° C. to restore to a liquid state, then MEM was added at room temperature, and then centrifuged at 3000 rpm/5 min. The supernatant was removed after centrifugation, and 1 ml of MEM was added to resuspend the cells, then the number of cells were counted by using a cell counter (ADAM MC Auto Cell Counter).

TABLE 3

| Example/Comparative example | Methyl cellulose (parts by weight) | Hydrogel (parts by weight) | Atelocollagen (parts by weight) | Gelatin (parts by weight) | Water (parts by weight) | Cell return ratio | Cell viability (%) | Multiple of available cells |
|---|---|---|---|---|---|---|---|---|
| Example 1 | 266.67 | 0.33 | 1 | 3.33 | 3062 | 5 | 82.44 | 4.58 |
| Example 2 | 266.67 | 0.33 | 1 | 6.67 | 3059 | 4 | 92.69 | 3.65 |
| Example 3 | 266.67 | 0.33 | 1 | 10 | 3055 | 3 | 84.66 | 3.82 |
| Comparative example 1 | 266.67 | 0.33 | 0 | 3.33 | 3063 | 3 | 90.07 | 4.21 |
| Comparative example 2 | 266.67 | 0.33 | 1 | 0 | 3065 | 7 | 50.44 | 3.54 |

The cell return ratio was calculated as: [number of cell return with ECM factor added]/[number of cell return without ECM factor added], cell survival rate was calculated as: [number of surviving cells]/[total number of cells]×100%, the multiple of available cells was calculated as: [cell survival rate (%)]×[cell return ratio]. According to the results in Table 3, it is known that the composition of collagen and gelatin with a specific content ratio (Examples 1~3) has a better cell return performance. It should be understood that although the cell survival rate and the multiple of available cells of Comparative example 1 are also high, but the cell return of Comparative example 1 is relatively low, the morphology of cell growth is not good, and the total number of viable cells is also less, therefore, its survival rate does not seem to fully reflect the actual growth of cells.

Examples 4~8 and Comparative Examples 3~6

The compositions of Examples 4~8 and Comparative examples 3~6 were prepared in a similar manner to the foregoing Examples 1~3 and Comparative examples 1~2, according to the content of methyl cellulose, hydrogel, atelocollagen and gelatin shown in Table 4. In detail, the mixture of methyl cellulose, hydrogel and ultrapure water was gelled at 37° C. and dried for 1 hour, then the mixture of atelocollagen and gelatin was added, and placed in an incubator at 37° C. for 6~12 hours, NCTC clone 929 cells and medium as mentioned above were added afterwards. Then, cultured by aeration in 95% air and 5% carbon dioxide for 3/5/7 days, and after the 3/5/7 days, the cells were recovered and tested for cell viability. The calculation method of cell viability is the same as mentioned above, and the results are shown in the Table 4.

TABLE 4

| Example/Comparative example | Methyl cellulose (parts by weight) | Hydrogel (parts by weight) | atelocollagen (parts by weight) | Gelatin (parts by weight) | Water (parts by weight) | Cell viability (%) | | |
|---|---|---|---|---|---|---|---|---|
| | | | | | | 3 days | 5 days | 7 days |
| Comparative example 3 | 166.67 | 0.033 | 1 | 3.33 | 3162 | 92.69 | 92.97 | 0.00 |
| Example 4 | 166.67 | 0.33 | 1 | 3.33 | 3162 | 90.78 | 76.69 | 78.13 |
| Comparative example 4 | 266.67 | 0.033 | 1 | 3.33 | 3062 | 81.94 | 73.75 | 50.68 |
| Example 5 | 266.67 | 0.33 | 1 | 3.33 | 3062 | 98.89 | 92.15 | 95.08 |
| Example 6 | 266.67 | 3.33 | 1 | 3.33 | 3059 | 97.87 | 94.37 | 90.91 |
| Example 7 | 266.67 | 33.33 | 1 | 3.33 | 3029 | 87.23 | 92.96 | 91.87 |
| Comparative example 5 | 266.67 | 66.67 | 1 | 3.33 | 2996 | 20.23 | 49.22 | 63.11 |
| Example 8 | 333.33 | 33.33 | 1 | 3.33 | 2962 | 73.64 | 60.24 | 96.75 |
| Comparative example 6 | 333.33 | 66.67 | 1 | 3.33 | 2929 | 22.97 | 40.94 | 63.77 |

Comparative Examples 7~10

The compositions of Comparative examples 7~10 were prepared according to the content of Pluronic® F-127 (average molecular weight of 12600 or more) (purchased from SIGMA manufacturer) shown in Table 5. In detail, Pluronic® F-127 and ultrapure water were mixed and stood in a 37° C. incubator for 6~24 hours, then the mixture of 1 part by weight of atelocollagen and 3.33 parts by weight of gelatin was added, and placed in an incubator at 37° C. for 6~12 hours, NCTC clone 929 cells and medium as mentioned above were added afterwards. Then, cultured by aeration in 95% air and 5% carbon dioxide for 3/5/7 days, and after the 3/5/7 days, the cells were recovered and tested for cell viability. The calculation method of cell viability is the same as mentioned above, and the results are shown in the Table 5.

TABLE 5

| Comparative example | Pluronic® F-127 (parts by weight) | Atelocollagen (parts by weight) | Gelatin (parts by weight) | Water (parts by weight) | Cell viability (%) | | |
|---|---|---|---|---|---|---|---|
| | | | | | 3 days | 5 days | 7 days |
| 7 | 3.3 | 1 | 3.33 | 3226 | 90.96 | 38.47 | 0 |
| 8 | 166.67 | 1 | 3.33 | 3162 | 85.70 | 0 | 0 |
| 9 | 333.33 | 1 | 3.33 | 2996 | 53.21 | 20.59 | 0 |
| 10 | 666.67 | 1 | 3.33 | 2662 | 99.00 | 31.85 | 0 |

According to the results in Table 4 and Table 5, it is known that the cell viability of the composition using methylcellulose, hydrogel, collagen, and gelatin is significantly higher compared to the composition using Pluronic® F-127 (Comparative Examples 7-10) by day 7.

Example 9/Comparative Examples 11~13

The compositions of Example 9 and Comparative examples 11-13 were prepared according to the contents shown in Table 6. Specifically, in Example 9, the mixture of methyl cellulose, hydrogel and ultrapure water was gelled at 37° C. and dried for 1 hour, then the mixture of atelocollagen and gelatin was added; in Example 11, the mixture of methyl cellulose and ultrapure water was gelled at 37° C. and dried for 1 hour, then the mixture of atelocollagen and gelatin was added; in Comparative example 12, the mixture of collagen, gelatin and ultrapure water was gelled at 37° C. and dried for 1 hour; in Comparative example 13, Pluronic® F-127 and ultrapure water were mixed, then the mixture of atelocollagen and gelatin was added. Next, the above composition was stood in an incubator at 37° C. for 6-12 hours and then the cells and the medium were added. Then, cultured by aeration in 95% air and 5% carbon dioxide for 4 days, and after the 4 days, the cells were recovered and the cell doubled ratio was calculated. The results are shown in Table 6.

TABLE 6

| Example/ Comparative example | methyl cellulose (parts by weight) | hydrogel (parts by weight) | atelocollagen (parts by weight) | gelatin (parts by weight) | Pluronic® F-127 (parts by weight) | water (parts by weight) | cell doubled ratio |
|---|---|---|---|---|---|---|---|
| Example 9 | 266.67 | 0.33 | 1 | 3.33 | 0 | 3062 | 1.475 |
| Comparative example 11 | 266.67 | 0 | 1 | 3.33 | 0 | 3062 | 1.168 |
| Comparative example 12 | 0 | 0 | 1 | 3.33 | 0 | 3329 | 1 |
| Comparative example 13 | 0 | 0 | 1 | 3.33 | 666.67 | 2662 | 0.091 |

The cell doubled ratio was calculated as: [multiple of cell growth of control group]/[multiple of cell growth of comparison group]. The comparison group was Comparative example 12 with a cell doubled ratio of 1, and the other groups were control groups. The higher the value of the cell doubled ratio, the more favorable it is for cell growth. According to the results in Table 6, it is known that Example 9 with specific components and ratios has a higher cell doubled ratio than Comparative Examples 11~13, which is favorable for increasing the number of cells.

Cell Staining Experiment

The cell staining experiment was performed using the composition of foregoing Test example 6 and Example 9. After standing in a 37° C. incubator for 2~6 hours, NCTC clone 929 cells and medium as mentioned above were added afterwards, and the cells were stained and observed after incubation for 1 day/4 days. In detail, the cell culture medium was removed after culturing for 1 day/4 days, 1 ml of PBS was added for washing, then the reagents were added according to the instructions of the LIVE/DEAD™ Viability/Cytotoxicity Kit. The reagents were removed after waiting for 2 hours, and then the Nikon Eclipse Ti microscope was used for observation.

Figure 5A:
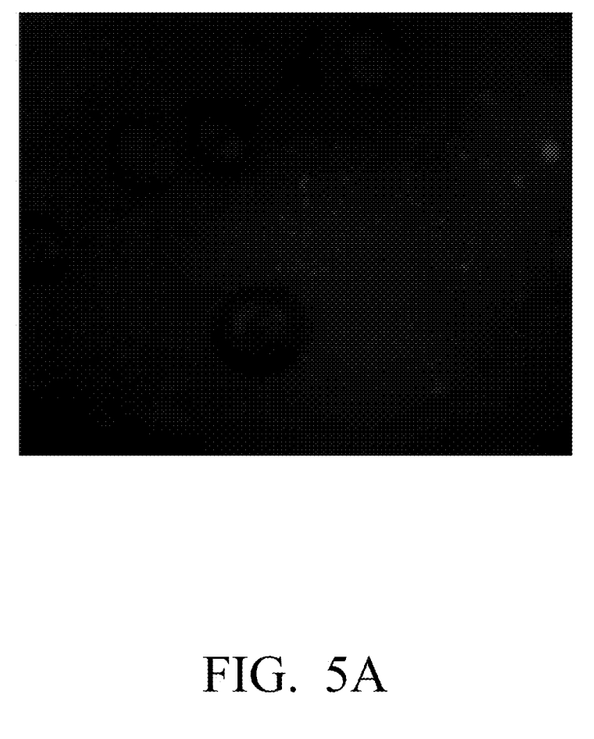
FIG. 5A and FIG. 5B show the cell staining results of the temperature-sensitive cell culture composition according to some embodiments of the present disclosure.
Figure 5B:
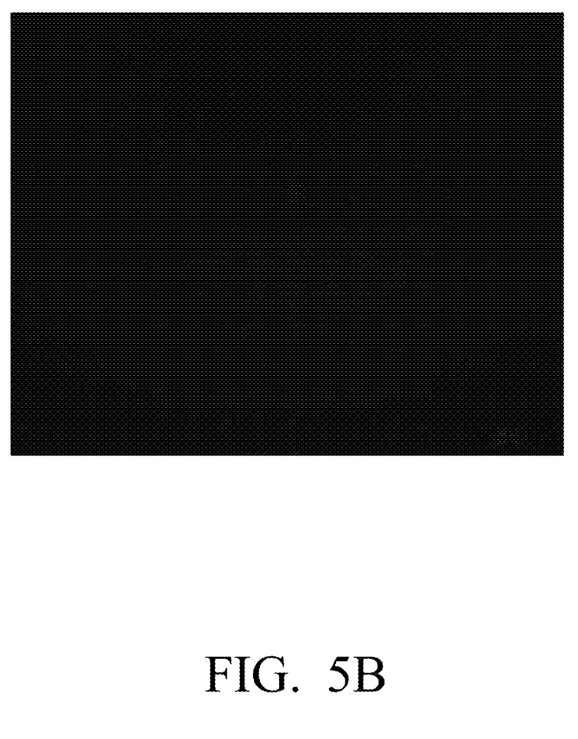
Figure 6A:
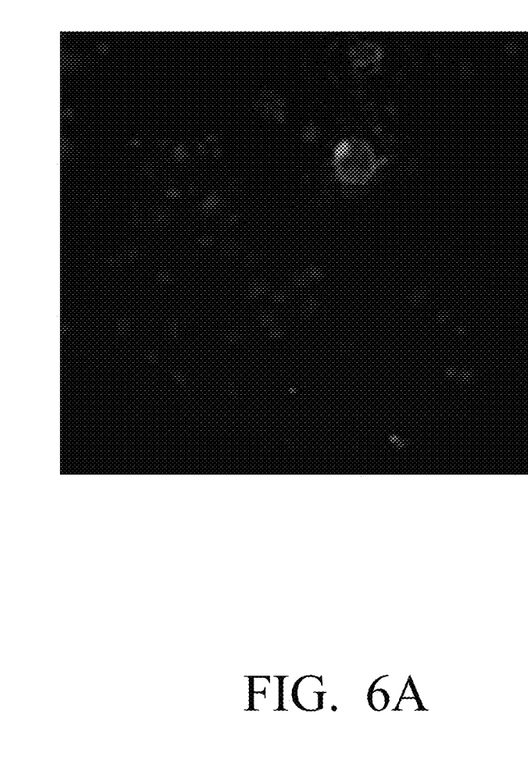
FIG. 6A and FIG. 6B show the cell staining results of the temperature-sensitive cell culture composition according to some embodiments of the present disclosure.
Figure 6B:
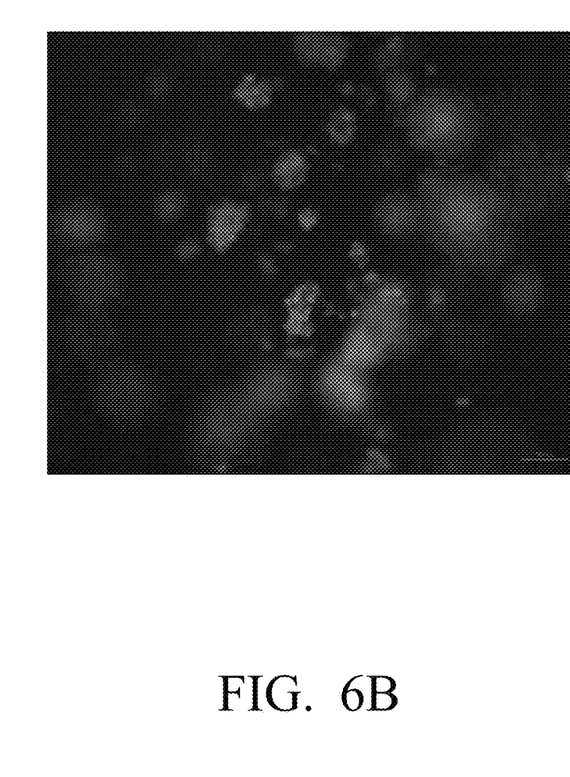

The cell staining results of the composition formed by the formula shown in Test example 6 after culturing for 1 day and 4 days are shown in FIG. 5A and FIG. 5B respectively. As shown in FIG. 5A, after the composition of only methylcellulose and hydrogel was cultured for 1 day, the amount of red fluorescence was greater than the amount of green fluorescence, which means that the number of dead cells was greater than the number of viable cells. As shown in FIG. 5B, after the composition of only methylcellulose and hydrogel was cultured for 4 days, almost no fluorescence was observed since the cells had been dead for a long time. Moreover, the cell staining results of the composition formed by the formula shown in Test example 9 after culturing for 1 day and 4 days are shown in FIG. 6A and FIG. 6B respectively. As shown in FIG. 6A, culturing with the composition containing methyl cellulose, hydrogel, collagen and gelatin, many cells survived (green fluorescence) after 1 day of culture. As shown in FIG. 6B, after 4 days of culture, the number of surviving cells increased significantly compared to the first day of culture.

In summary, according to some embodiments of the present disclosure, the temperature-sensitive cell culture composition with a specific formula has good biocompatibility and temperature-sensitive phase transition properties, and is easy to operate in cell culture experiments and subsequent applications. Also, it can be used directly as a cell carrier without separation and purification steps, so that the damage to cells caused by traditional cell separation and purification steps was avoided, and the convenience of related applications after cell culture can be effectively improved as well.

It will be apparent to those having ordinary skilled in the art that various modifications and variations can be made to the disclosed embodiments without departing from the scope or spirit of the disclosure. It is intended that the specification and examples be considered as exemplary only, with the true scope of the disclosure being indicated by the following claims and their equivalents. In addition, the protection scope of the present disclosure is not limited to the manufacturing process, machinery, manufacturing, material composition, device, method, and steps in the specific embodiments described in the specification. The current or future developed processes, machines, manufacturing, material composition, devices, methods, and steps can be understood by those having ordinary skilled in the art from the content of the present disclosure, as long as they may be implemented substantially the same functions or obtain substantially the same results in the embodiments described herein, they may all be used according to the present disclosure. Therefore, the protection scope of the disclosure includes the foregoing manufacturing process, machinery, manufacturing, material composition, device, method, and steps. It is intended that the specification and examples be considered as exemplary only, with a true scope of the disclosure being indicated by the following claims and their equivalents.

What is claimed is:

1. A temperature-sensitive cell culture composition, comprising:
    a hydrogel, wherein the hydrogel has a structure represented by Formula (I) or Formula (II) shown as follows:

A-B-BOX-B-A,            Formula (I); or B-A-B-(BOX-BAB)n-BOX-B-A-B,        Formula (II), wherein the polymer block A is a hydrophilic polyethylene glycol polymer, the polymer block B is a hydrophobic polyester polymer, BOX is a bifunctional group monomer of 2,2'-Bis(2-oxazoline) for coupling di-block of A-B or tri-block of B-A-B, and n is an integer greater than or equal to 0, and wherein an average molecular weight of the hydrogel is between 2000 and 6000,
    wherein the polymer block A comprises polyethylene glycol (PEG) or methoxy-poly(ethylene glycol) (mPEG), and the polymer block B comprises poly (lactide-co-glycolide) (PLGA), poly(propionic-co-lactic (PPLA), poly(valeric-co-lactic) (PVLA) or poly (caproic-co-lactic) (PCLA);
    a cellulose;
    a gelatin; and
    a collagen;
    wherein based on 1 part by weight of the collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight.

2. The temperature-sensitive cell culture composition as claimed in claim 1, wherein based on 1 part by weight of the collagen, a content of the hydrogel is between 0.33 parts by weight and 33 parts by weight, a content of the cellulose is between 166 parts by weight and 333 parts by weight, and a content of the gelatin is between 3 parts by weight and 10 parts by weight.

3. The temperature-sensitive cell culture composition as claimed in claim 1, wherein the collagen comprises atelocollagen.

4. The temperature-sensitive cell culture composition as claimed in claim 1, wherein the cellulose comprises methyl cellulose.

5. The temperature-sensitive cell culture composition as claimed in claim 1, further comprising a medium, the medium comprises amino acids, vitamins, serum, antibiotics or a combination thereof.

6. The temperature-sensitive cell culture composition as claimed in claim 1, further comprising water.

7. A method for using a temperature-sensitive cell culture composition, comprising:
    adding a cell to the temperature-sensitive cell culture composition as claimed in claim 1 at a first temperature; and
    performing cell culture at a second temperature.

8. The method for using a temperature-sensitive cell culture composition as claimed in claim 7, wherein the temperature-sensitive cell culture composition is a liquid at the first temperature, the temperature-sensitive cell culture composition is a gel at the second temperature.

9. The method for using a temperature-sensitive cell culture composition as claimed in claim 7, wherein the first temperature is between 0° C. and 32° C.

10. The method for using a temperature-sensitive cell culture composition as claimed in claim 7, wherein the second temperature is between 33° C. and 40° C.

11. The method for using a temperature-sensitive cell culture composition as claimed in claim 7, further comprising:
    after culturing cells at the second temperature, loading the temperature-sensitive cell culture composition into an appliance at the first temperature.

12. The method for using a temperature-sensitive cell culture composition as claimed in claim 11, further comprising:
    applying the temperature-sensitive cell culture composition to a subject by the appliance.

13. The method for using a temperature-sensitive cell culture composition as claimed in claim 7, wherein the cell comprises a stem cell, an immune cell, a somatic cell or a combination thereof.

14. A method for forming a temperature-sensitive cell culture composition, comprising:
    mixing a hydrogel and a cellulose at a first temperature, allowing to stand for a first time interval at a second temperature to form a gel substrate, wherein the hydrogel has a structure represented by Formula (I) or Formula (II) shown as follows:

A-B-BOX-B-A,            Formula (I); or B-A-B-(BOX-BAB)n-BOX-B-A-B,        Formula (II), wherein the polymer block A is a hydrophilic polyethylene glycol polymer, the polymer block B is a hydrophobic polyester polymer, BOX is a bifunctional group monomer of 2,2'-Bis(2-oxazoline) for coupling di-block of A-B or tri-block of B-A-B, and n is an integer greater than or equal to 0, and wherein an average molecular weight of the hydrogel is between 2000 and 6000,
    wherein the polymer block A comprises polyethylene glycol (PEG) or methoxy-poly(ethylene glycol) (mPEG), and the polymer block B comprises poly (lactide-co-glycolide) (PLGA), poly(propionic-co-lactic (PPLA), poly(valeric-co-lactic) (PVLA) or poly (caproic-co-lactic) (PCLA; and adding a mixture of a collagen and a gelatin to the gel substrate;

wherein based on 1 part by weight of the collagen, a content of the hydrogel is between 0.03 parts by weight and 60 parts by weight, a content of the cellulose is between 150 parts by weight and 360 parts by weight, and a content of the gelatin is between 1 part by weight and 12 parts by weight.

15. The method for forming a temperature-sensitive cell culture composition as claimed in claim 14, wherein after the mixture of the collagen and the gelatin is added to the gel substrate, it is allowed to stand at the second temperature for a second time interval, so that the mixture of the collagen and the gelatin forms a gel layer.

16. The method for forming a temperature-sensitive cell culture composition as claimed in claim 15, further comprising:

adding a culture medium on the gel layer, wherein the culture medium is a liquid.

\* \* \* \* \*